United States Patent
Yamada et al.

(10) Patent No.: US 9,067,066 B2
(45) Date of Patent: Jun. 30, 2015

(54) PARTICLE BEAM THERAPY DEVICE AND PARTICLE BEAM THERAPY DEVICE OPERATION METHOD

(75) Inventors: Yukiko Yamada, Tokyo (JP); Hisashi Harada, Tokyo (JP); Taizo Honda, Tokyo (JP); Masahiro Ikeda, Tokyo (JP); Kazushi Hanakawa, Tokyo (JP); Toshihiro Otani, Tokyo (JP); Tadashi Katayose, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 0 days.

(21) Appl. No.: 14/356,629

(22) PCT Filed: Mar. 27, 2012

(86) PCT No.: PCT/JP2012/057894
§ 371 (c)(1),
(2), (4) Date: Jul. 15, 2014

(87) PCT Pub. No.: WO2013/145117
PCT Pub. Date: Mar. 10, 2013

(65) Prior Publication Data
US 2014/0323793 A1    Oct. 30, 2014

(51) Int. Cl.
*G21K 5/04* (2006.01)
*A61N 5/10* (2006.01)
(52) U.S. Cl.
CPC ............ *A61N 5/1048* (2013.01); *A61N 5/1077* (2013.01)
(58) Field of Classification Search
USPC ............ 250/492.1, 492.3, 396 R, 397; 600/1; 315/500, 501, 502, 503, 504, 505, 506, 315/507
See application file for complete search history.

(56) References Cited

U.S. PATENT DOCUMENTS

| | | | |
|---|---|---|---|
| 6,683,318 B1 * | 1/2004 | Haberer et al. | 250/492.3 |
| 7,560,717 B2 * | 7/2009 | Matsuda et al. | 250/505.1 |
| 2009/0283702 A1 | 11/2009 | Umezawa et al. | |
| 2011/0233423 A1 * | 9/2011 | Balakin | 250/454.11 |
| 2011/0260074 A1 | 10/2011 | Honda et al. | |

FOREIGN PATENT DOCUMENTS

| | | |
|---|---|---|
| JP | 2007-132902 A | 5/2007 |
| JP | 2008-154627 A | 7/2008 |

(Continued)

OTHER PUBLICATIONS

International Search Report (PCT/ISA/210) mailed on Jun. 26, 2012, by the Japanese Patent Office as the International Searching Authority for International Application No. PCT/JP2012/057894.

*Primary Examiner* — Nicole Ippolito
(74) *Attorney, Agent, or Firm* — Buchanan Ingersoll & Rooney PC

(57) ABSTRACT

A control unit is provided with, a retaining section that retains a plurality of operation patterns each being a pattern of operation to be periodically repeated by an accelerator, the operation patterns having respective operation conditions adjusted for different emission times of an particle beam, to cause a deflection electromagnet in the accelerator to have an intended magnetic field intensity even under a presence of a hysteresis; a reading section for a plurality of slices of an irradiation target in a depth direction, which reads an irradiation condition for each of the slices; a selection section that selects the operation pattern suitable for each of the slices, on the basis of the read irradiation condition; and a main control section that controls, for each of the slices, the accelerator on the basis of the selected operation pattern and an irradiation device on the basis of the irradiation condition.

9 Claims, 7 Drawing Sheets

(56) References Cited

FOREIGN PATENT DOCUMENTS

| | | |
|---|---|---|
| JP | 2008-226740 A | 9/2008 |
| JP | 2009-273632 A | 11/2009 |
| JP | 2010-201099 A | 9/2010 |
| JP | 2010-238463 A | 10/2010 |
| WO | WO 2011/092815 A1 | 8/2011 |
| WO | WO 2011/121762 A1 | 10/2011 |

* cited by examiner

OP-S

OP-L

PARTICLE BEAM THERAPY DEVICE AND PARTICLE BEAM THERAPY DEVICE OPERATION METHOD

TECHNICAL FIELD

The present invention relates to a particle beam therapy for treating a diseased portion of a patient by irradiating it with a particle beam, and in particular, to a particle beam therapy system that performs irradiation for each of different-depth layers, and a method of operating the same.

BACKGROUND ART

A particle beam therapy, which is a treatment of a deceased tissue by irradiating it with a particle beam to thereby damage the tissue, is a part of broad-sense radiation therapy. However, unlike a y-ray, an X-ray or like other ray, when a particle beam such as a proton beam, a heavy ion beam, etc., goes forward in a substance, its velocity decreases due to receiving resistance inversely proportional to the square of the velocity, and the beam rapidly stops after becoming a certain velocity or less, and at that time an imparted dose becomes highest. Accordingly, in the particle beam therapy, it is possible to control a range of irradiation in a depth direction by adjusting the velocity (energy) at the time of going into the body. Thus, in the particle beam therapy, it is possible to perform so-called layer-stacking conformal irradiation which is irradiation that makes the imparted dose corresponding to the three-dimensional shape of the deceased site in such a manner that the deceased site is partitioned in an in-body depth direction and an irradiation shape is formed for each partitioned layer (slice).

However, because of a relationship called as Bragg's curve between a depth and a dose distribution, when irradiation is made matching the peak (Bragg's peak) with a given slice, the imparted dose in a portion other than the slice becomes larger at the shallow side from the slice than at the deep side therefrom. Thus, when performing layer-stacking conformal irradiation, the irradiation time set for a shallow slice becomes shorter than the irradiation time set for a deep slice (see, for example, Patent Document 1). Meanwhile, in the operation of an accelerator that is fundamentally a beam source of the particle beam, although the particle beam is emitted by periodically repeating steps including injection, acceleration, emission and deceleration, the operation period is generally fixed. Thus, in a case where the operation period is matched with a shallow slice, when a deep slice is irradiated, the irradiation will be made extending over a plurality of the operation periods, so that a waiting time increases over the operation periods, resulting in extension of a treatment time. Instead, in a case where it is matched with a deep slice, when a shallow slice is irradiated, it is necessary to wait even after completion of the irradiation until completion of the operation period, resulting anyhow in extension of the treatment time.

Thus, it is considered to incorporate, for example, an operation method of a particle beam accelerator in which energy is changed in the middle of the operation period (see, for example, Patent Document 2), or a technique of changing an operation pattern (corresponding to the operation period) in the operation according to an amount of electric charge in the accelerator (see, patent Document 3).

CITATION LIST

Patent Document

Patent Document 1: Japanese Patent Application Laid-open No. 2010-201099 (paragraph 0018, FIG. 5, FIG. 6)

Patent Document 2: Japanese Patent Application Laid-open No. 2008-226740 (paragraphs 0041 to 0043, FIG. 1, FIG. 2)

Patent Document 3: Japanese Patent Application Laid-open No. 2010-238463 (paragraphs 0052 to 0055, FIG. 10)

SUMMARY OF THE INVENTION

Problems to be Solved by the Invention

However, the operation period has to be determined by adjusting, in consideration also a magnetic aftereffect etc., a detailed operation condition in each step so that the accelerator can stably emit the particle beam. Thus, when the period or the energy is changed in the middle of the operation without careful consideration, since a hysteresis of a deflection electromagnet changes, for example, it is difficult to keep a trajectory of the particle beam in the setup state. Accordingly, in an irradiation method in which a particle beam is required to be supplied with an accurate trajectory, such as, for example, a scanning method in which an irradiation field is formed by scanning, it becomes difficult to perform accurate irradiation according to a treatment plan.

This invention has been made to solve the problem as described above, and an object thereof is to provide a particle beam therapy system which can make the treatment time shorter and can perform accurate irradiation.

Means for Solving the Problems

A particle beam therapy system of the invention is characterized by comprising: an accelerator having a deflection electromagnet using a core of a magnetic material, that emits a particle beam after adjusting it to have a given energy; an irradiation device that irradiates an irradiation target with the particle beam supplied from the accelerator, according to a shape of the target; and a control unit that controls the accelerator and the irradiation device in their cooperative manner; wherein the particle beam therapy system is provided with: an operation pattern retaining section that retains a plurality of operation patterns each given as a pattern of operation to be periodically repeated by the accelerator, said operation patterns having respective operation conditions adjusted to have different times that allow emission of the particle beam, and to cause the deflection electromagnet in the accelerator to have an intended magnetic field intensity even under a presence of hysteresis of the magnetic material; an irradiation condition reading section for a plurality of slices resulted from partitioning the irradiation target in a depth direction, that reads an irradiation condition for each of the slices; an operation pattern selection section that selects the operation pattern suitable for said each of the slices from among the plurality of operation patterns, on the basis of the irradiation condition read by the irradiation condition reading section; and a main control section that controls, for each of the slices, the accelerator on the basis of the selected operation pattern and the irradiation device on the basis of the irradiation condition.

Effect of the Invention

According to the particle beam therapy system of the invention, the operation patterns that have been adjusted in advance and have different times that allow emission of the particle beam, are used differently depending on the irradiation condition for the slice. Thus, it is possible to achieve a particle beam therapy system that can make the treatment time shorter and can control the trajectory of the particle beam accurately.

MODES FOR CARRYING OUT THE INVENTION

Embodiment 1

Figure 1A:
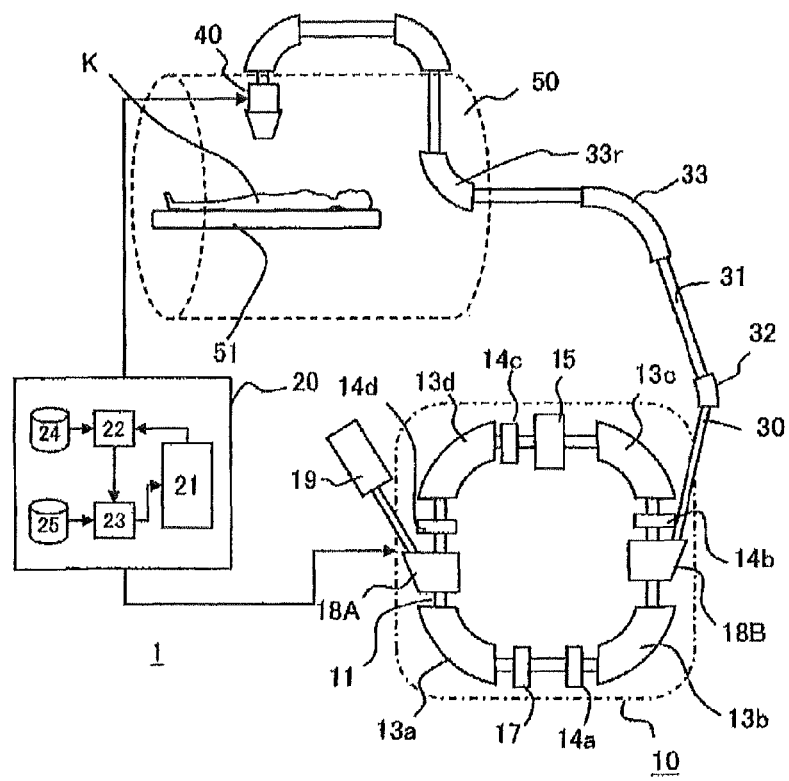
FIG. 1A and FIG. 1B comprise an overall view for illustrating a configuration of a particle beam therapy system and graphs showing two operation patterns of an accelerator, according to Embodiment 1 of the invention.
Figure 1B:
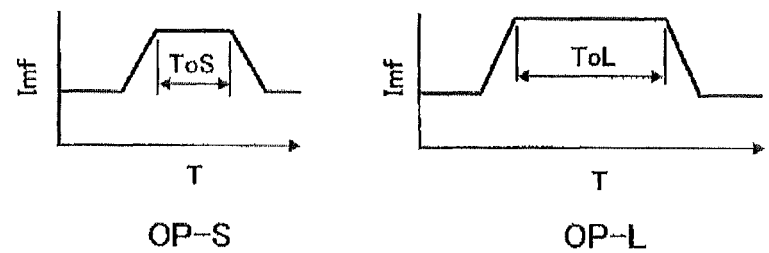
Figure 2:
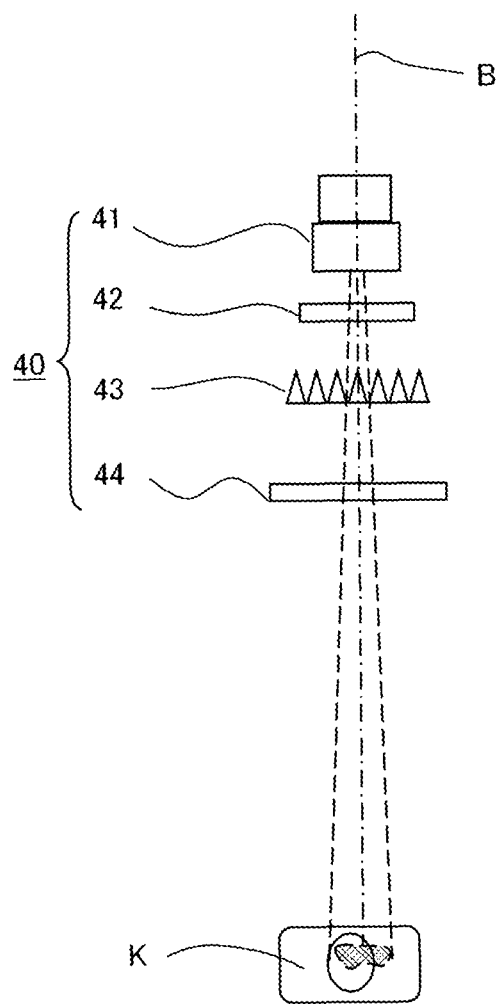
FIG. 2 is a diagram for illustrating a configuration of an irradiation device in the particle beam therapy system according to Embodiment 1 of the invention.
Figure 3A:
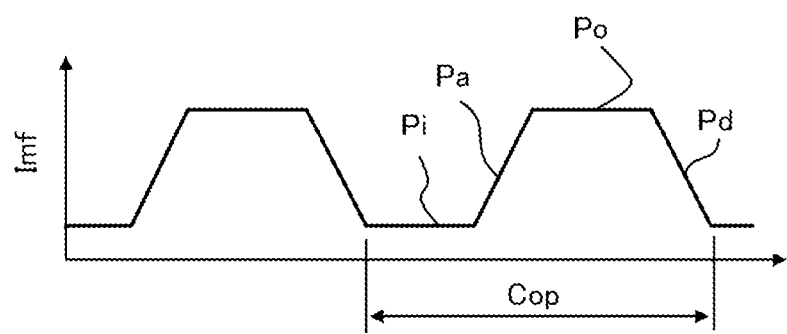
FIG. 3A and FIG. 3B comprise a graph for illustrating an operation pattern of the accelerator of the particle beam therapy system according to Embodiment 1 of the invention, and a graph showing a hysteresis loop of a deflection electromagnet that constitutes the accelerator operated in that operation pattern.
Figure 3B:
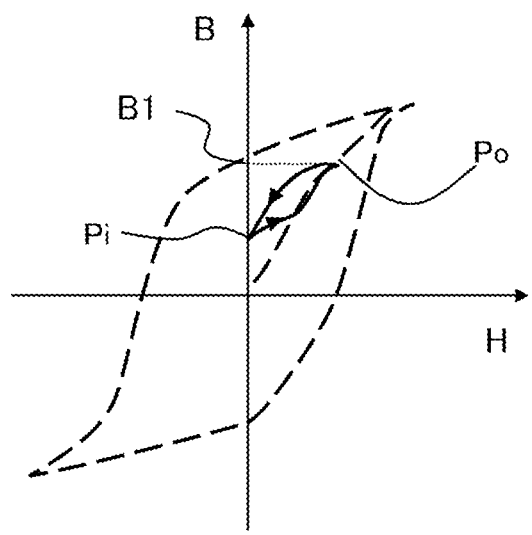
Figure 4:
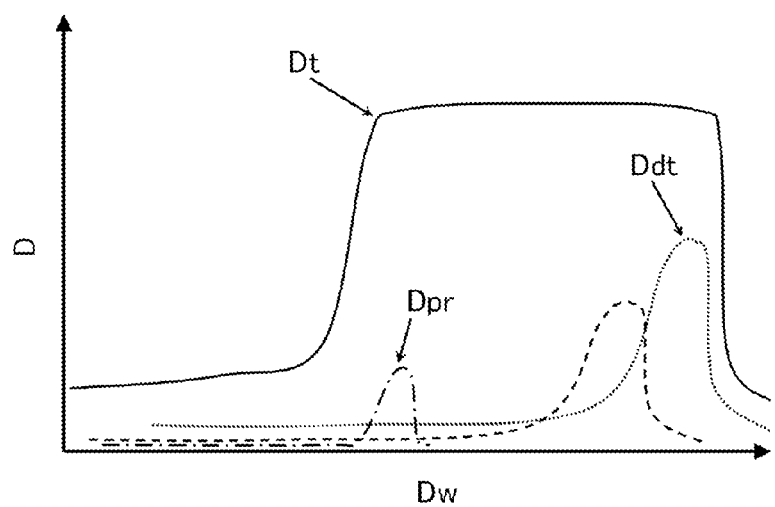
FIG. 4 is a graph showing a relationship between a depth from a body surface and a dose, according to layer-stacking conformal irradiation.
Figure 5:
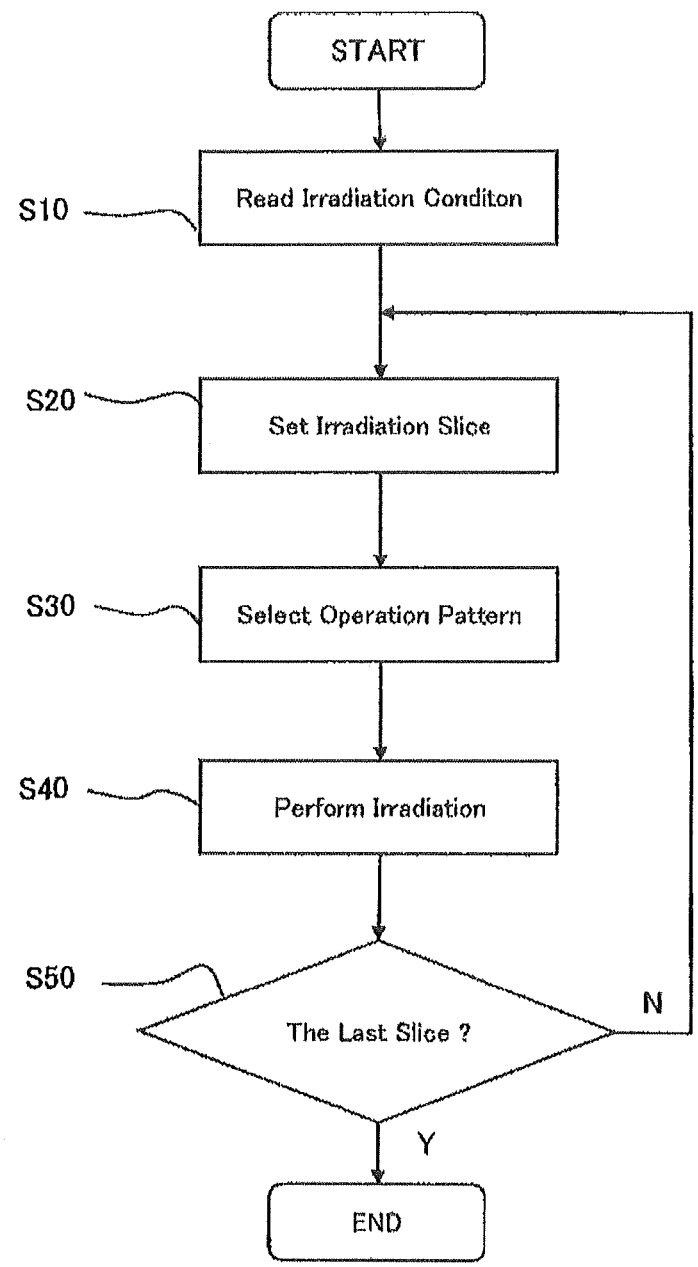
FIG. 5 is a flowchart for illustrating a method of operating the particle beam therapy system according to Embodiment 1 of the invention.
Figure 6A:
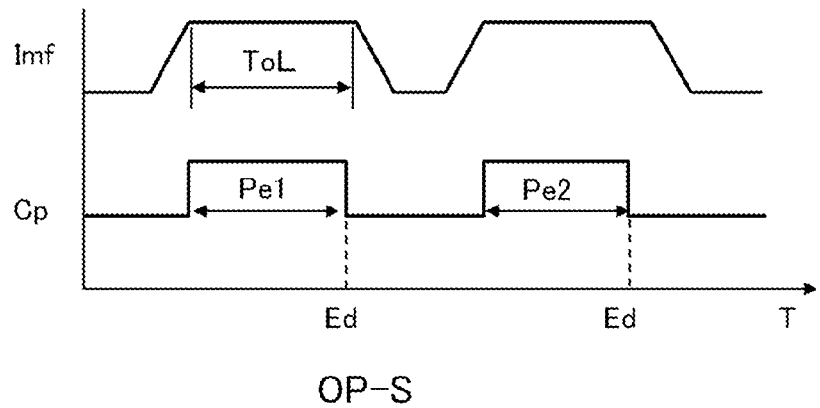
FIG. 6A and FIG. 6B are graphs each for illustrating an irradiation condition in an operation period when an operation pattern is selected according to a depth of a slice.
Figure 6B:
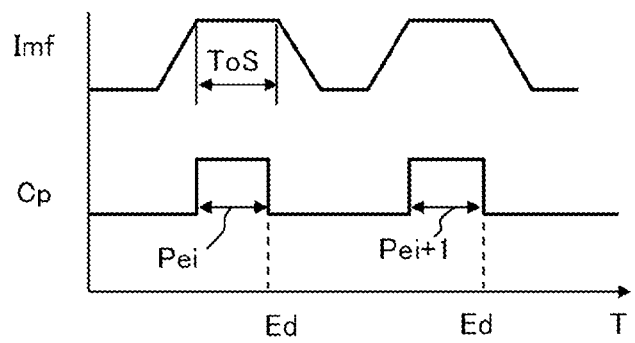

Hereinafter, a configuration and operation of a particle beam therapy system according to Embodiment 1 of the invention will be described. FIG. 1 to FIG. 6 are for illustrating the particle beam therapy system according to Embodiment 1 of the invention, in which FIG. 1(a) and FIG. 1(b) are a diagram showing an overall configuration (a) of the particle beam therapy system and graphs for illustrating previously-prepared two operation patterns (b) of an accelerator that is a beam source of the particle beam therapy system. FIG. 2 is a diagram for illustrating a configuration of an irradiation device. FIG. 3(a) and FIG. 3 (b) are for illustrating a periodic operation pattern of the accelerator and a hysteresis of a magnetic core in that period, in which FIG. 3(a) is a graph showing a variation in magnetic field of a deflection electromagnet, and FIG. 3(b) is a graph showing a hysteresis loop of the deflection electromagnet that constitutes the accelerator at the operation in the operation pattern of (a). FIG. 4 is a graph for a case of applying layer-stacking conformal irradiation, showing a relationship between a depth from a body surface and a dose by the irradiation for each slice and a relationship between a depth from the body surface and an accumulated dose from these doses. FIG. 5 is a flowchart for illustrating a method of operating the particle beam therapy system. Further, FIG. 6(a) and FIG. 6(b) are graphs each for illustrating an irradiation condition in an operation period when an operation pattern is selected according to a depth of a slice, in which FIG. 6(a) shows a case of selecting a short period operation pattern, and FIG. 6(b) is a case of selecting a long period operation pattern.

As shown in FIG. 1(a), a particle beam therapy system 1 according to Embodiment 1 includes, as a source of supplying a particle beam B, a circular accelerator 10 which is a cyclo-tron (hereinafter, referred to simply as "accelerator"); a transport system 30 for transporting the particle beam B supplied from the accelerator 10; an irradiation device 40 for irradiating a patient with the particle beam B transported by the transport system 30; a treatment room 50 provided with the irradiation device 40; and a control unit 20 for controlling these respective instruments. In the control unit 20, as shown in FIG. 1(b), there are retained as data, at least two operation patterns having different operation periods and each having operation parameters for individual steps that are adjusted in advance, so that irradiation is made after selecting the operation pattern according to an irradiation time required for the slice. Before describing a detailed configuration and control of the control unit 20, main instruments constituting the particle beam therapy system will be described.

<Accelerator>

The accelerator 10 includes a vacuum duct 11 that provides a trajectory channel through which the particle beam B goes around; an injection device 18A for injecting the particle beam B supplied from a pre-accelerator 19 into the round trajectory; deflection electromagnets 13a to 13d (referred to collectively as numeral 13) for deflecting a trajectory of the particle beam B so that the particle beam B goes around along the round trajectory in the vacuum duct 11; convergence electromagnets 14a to 14d (referred to collectively as numeral 14) that cause the particle beam B formed on the round trajectory to converge so as not to diverge; a high-frequency acceleration cavity 15 that applies to the particle beam B going around, a high frequency voltage synchronous with the beam to thereby accelerate the beam; an emission device 18B for taking out from the accelerator 10, the particle beam B accelerated in the accelerator 10 so as to emit it toward the transport system 30; and a sextupole magnet 17 that excites resonance in the round trajectory of the particle beam B for emitting the particle beam B from the emission device 183. As described later, since the electromagnets of these types each use a core of magnetic material, a hysteresis emerges according to a history of the magnetic field intensity.

There are provided not-shown devices for controlling the respective parts, such as, for the deflection electromagnets 13, deflection electromagnet control devices that control currents for exciting the deflection electromagnet 13; and for the high-frequency acceleration cavity 15, a high frequency source for supplying the high frequency voltage to the high-frequency acceleration cavity 15 and a high-frequency control device for controlling the high frequency source. There is further provided in the control unit 20, an accelerator control unit or the like that performs overall control of the accelerator 10 by controlling the deflection electromagnet control devices, the high-frequency control device, convergence electromagnets 14 and like other components.

Further, although the pre-accelerator 19 is illustrated as a single device in the figure for simplification's sake, it is actually provided with an ion source (ion beam generating device) for generating charged particles (ions) of proton, carbon (heavy particle) or the like, and a linear accelerator system that initially accelerates the generated charged particles. Here, the charged particles that has entered the accelerator 10 from the pre-accelerator 19 is accelerated by a high frequency electric field up to approx. 70% to 80% of the light velocity while being bent by the magnets.

<Transport System>

The particle beam B accelerated by the accelerator 10 is emitted to the transport system 30 called as HEBT (High Energy Beam Transport) system. The transport system 30 includes a vacuum duct 31 that provides a transport channel of the particle beam B; a switching electromagnet 32 that is a switching device for switching the beam trajectory of the particle beam B; and a deflection electromagnet 33 that deflects the particle beam B by a predetermined angle. The particle beam B that goes forward in the vacuum duct 31 after receiving a given energy by the accelerator 10 and emitted from the emission device 18B, is switched as necessary by the switching electromagnet 32 to a transport channel directed toward another treatment device which is not shown, and is guided to an irradiation device 40 provided in a specified treatment room 50.

<Irradiation Device>

The irradiation device 40 is a device that irradiates a deceased site of a patient K with the particle beam B supplied from the transport system 30 after forming the beam into an irradiation field according to the size and depth of the deceased site. Although there are plural methods for forming the irradiation field, in this embodiment, description will be made citing a case of using a scanning irradiation method that forms the irradiation field by scanning the particle beam B. Note that, as compared to a broad irradiation method that forms the irradiation field by means of a physical limiter, according to the scanning irradiation method, an accuracy of the trajectory, in particular, at the time of the entrance, largely affects an accuracy of the irradiation field to be formed. Thus, the accuracy of the trajectory of the supplied particle beam B may result in giving a large influence on whether or not the irradiation field can be formed accurately to thereby achieve the imparted dose according to the treatment plan.

As shown in FIG. 2, the irradiation device 40 includes a scanning electromagnet 41 that forms the irradiation field by scanning the particle beam B supplied from the beam source; a scatterer 42 that is formed of lead and scatters the particle beam B; a ridge filter 43 that is formed of aluminum or the like and spreads the width of the Bragg's peak depending on the thickness of the irradiation target; and a range shifter 44 that attenuates the energy of the particle beam B by a predetermined amount.

<Treatment Room>

The treatment room 50 is a room for performing a therapy by actually irradiating the patient K with the particle beam B, and the same is applied basically to another treatment room 50 that is not shown in the figure but is placed down a branch from the switching device 32, whereby the irradiation device 40 described above is provided in each treatment room 50. Note that in the figure, there is shown a case where the treatment room 50 is a rotating irradiation room 50 (called also as a rotary gantry) in which the irradiation device 40 with a portion from a deflection electromagnet 33r is rotatable as a whole about the patient K (treatment table 51) to thereby freely set an irradiation angle of the particle beam B to the patient K. Generally, for the single accelerator 10, a horizontal irradiation room 50 that irradiates with the particle beam B in a horizontal direction from the irradiation device 40, the patient fixed to the treatment table 51 whose angle and position is freely settable, and/or any other different type of treatment room 50, are provided in a plurality.

<Control Unit>

As a control system for the aforementioned system including a plurality of instruments (accelerator 10, transport system 30, irradiation device 40 for each treatment room 50, and the like), a hierarchical control system is used in many cases which comprises a sub-controller for solely controlling each of the instruments (sub systems) and a main-controller for supervising and controlling the whole. Also in the control unit 20 of the particle-beam-B therapy system according to Embodiment 1 of the invention, the configuration of the main-controller and the sub-controller is adopted. Functions in the control system are shared such that operations controllable in the sub systems are controlled by the sub-controller, and operations for controlling a plurality of said systems in their cooperative manner are controlled by the main-controller. Notwithstanding, in the description of the particle beam therapy system according to Embodiment 1 of the invention, the configuration is described as if the whole is controlled by the control unit 20 of a single structure, in order to focus on explanation of a function for selecting the operation pattern.

As shown in FIG. 1, the control unit 20 has a main control section 21 that performs controlling the whole; an irradiation condition retaining section 24 that retains a plurality of irradiation conditions, such as irradiation forms/doses and the like for a plurality of slices; an operation pattern retaining section 25 that retains a plurality of accelerator's operation patterns (to be referred to simply as operation patterns) having different periods; an irradiation condition reading section 22 that reads an irradiation condition for each slice in accordance with an order from the main control section 21 from among the irradiation conditions retained in the irradiation condition retaining section 24; and an operation pattern selection section 23 that selects for each slice, the operation pattern suitable for the irradiation condition for said each slice from among the operation patterns retained in the operation pattern retaining section 25.

As shown in FIG. 1(b), the operation patterns retained in the operation pattern retaining section 25 are at least, a short period pattern OP-S in which energy is small and an irradiation time (time that allows emission of the particle beam B) To is short, and a long period pattern OP-L in which energy is large and an irradiation time To is long. Note that, in FIG. 1(b), the abscissa represents time and the ordinate represents magnetic field intensity Imf of the deflection electromagnets 13 in the accelerator 10. This is because the magnetic field intensity Imf represents the energy of the particle beam B that goes around in the round trajectory, since the magnetic field intensity Imf of the deflection electromagnets 13 needs to be enhanced as the energy of the particle beam B becomes larger, namely, its velocity becomes higher, in order to bend the beam with the same curvature.

Here, the operation pattern of the accelerator 10 to be selected by the particle beam therapy system 1 will be described using FIG. 3 and FIG. 4. As shown in FIG. 3(a), in the operation of the accelerator 10, a plurality of steps are repeated as one period of Cop, said steps including an injection step Pi from the pre-accelerator 19, an acceleration step Pa of accelerating the particle beam B up to a predetermined velocity (energy), an emission step Po of emitting the particle beam B, and a deceleration step Pd of decelerating the velocity of the particle beam B. During these steps, a hysteresis of the deflection electromagnets 13 using the cores of magnetic material varies as shown in FIG. 3(b), due to change in magnetic field intensity Imf of the deflection electromagnets 13. By assessing influence of a magnetic aftereffect on this occasion in advance, the operation pattern is adjusted to achieve an intended magnetic field intensity even under the presence of the hysteresis.

For example, under the presence of hysteresis, even the same amount of electric current applied to the deflection electromagnets 13 does not always provide the same intensity of the magnetic field generated by the deflection electromagnets 13. Thus, the magnetic aftereffect is assessed in advance, to thereby prepare a table of current amounts that are to be applied to the deflection electromagnets 13 for every length of period in two successive periods and for every magnetic field intensity. Then, at the time of acceleration operation, an amount of current required for a given period, which is derived from a relationship between the length of period and the magnetic filed intensity in each of the given period and a one-previous period, is selected from the above table. Note that, here, assuming that the influence by a hysteresis in a two or more-previous period is little, the table is prepared for two successive periods; however, there is a case where the influence by a hysteresis in a two or more-previous period is not negligible. In this case, prepared is a table of current amounts that are to be applied to the deflection electromagnets 13 for every length of period in more than three successive periods and for every magnetic field intensity.

As far as using the thus-tuned operation pattern, an intended magnetic field intensity can be provided, so that the trajectory of the particle beam B is stabilized, and thus the emission can be made with an accurate trajectory. Meanwhile, as described in BACKGROUND ART, if the length of a step (in Patent Document, a length of the irradiation period Po) is changed carelessly or an operation pattern having been not tuned is used simply because the dose is fulfilled, the operation of the next period will be made under a different magnetic field intensity Imf due to a magnetic aftereffect, so that the trajectory of the particle beam B will vary, making it difficult to cause emission with an accurate trajectory.

Further, the method of using the thus pre-tuned operation pattern can be realized by increasing the number of operation patterns to be prepared and by adding a portion of selecting suitable operation pattern, with respect to a conventional method of using an operation pattern with a fixed period. Thus, as compared to the conventional control system, there is required a little change, resulting in simple and inexpensive configuration. Meanwhile, even if an operation system is fabricated that can arbitrarily change the length of step in consideration of the influence of a magnetic aftereffect, its control system becomes complex and the number of parts increases, so that the operation system becomes expensive.

On the other side, shown in FIG. 4 is a relationship, so called as Bragg's curve, between a depth and a dose distribution. In the figure, the abscissa represents a water depth Dw corresponding to a depth from the body surface, and the ordinate represents a dose D. Further, respective lines denotes a dose distribution Ddt in a deep (Distal) layer (slice) in the deceased site, a dose distribution Dpr in a shallow (Proximal) slice therein, and a dose distribution Dt obtained by accumulating a dose in every slice. As shown in the figure, in order to achieve a uniform dose distribution Dt overall from a shallow portion to a deep portion, the dose imparted in the shallow slice becomes smaller than the dose imparted in the deep slice. Namely, the irradiation time for the shallow slice becomes shorter than the irradiation time for the deep slice.

Thus, in the particle beam therapy system 1 according to Embodiment 1, as pre-tuned operation patterns, there are provided in the operation pattern retaining section 25, as shown in FIG. 1(b), the operation pattern OP-S for a shallow slice in which the energy is smaller and the time (irradiation time) To that allows emission of the particle beam B in one period is shorter than those for a deep slice, and the operation pattern OP-L for the deep slice in which the energy is larger and the irradiation time To is longer than those for the shallow slice.

Then, the operation pattern selection section 23 serves to select a suitable operation pattern from the two operation patterns depending on the irradiation condition (energy and irradiation time To) for each slice, and the control unit 20 controls the operation pattern of the accelerator 10 so that it operates according to the suitable operation pattern for each slice.

Note that, in the particle beam therapy system 1, generally, a work station or a computer is used as the control unit 20. Thus, respective parts constituting the control unit 20 are to be implemented by software etc., and therefore, they do not necessarily fall in a specific hardware. Thus, although they are collectively illustrated in the figure as the control unit 20, this does not mean that the control unit 20 is present as a physically single unified hardware.

Next, an operation of the particle beam therapy system 1 operated under such control will be described.

The particle beam B with the given energy, which is supplied to the irradiation device 40 from the accelerator 10 whose operation is being controlled by the operation pattern selected by the control unit 20, is in a state of a so-called pencil beam i.e. less than several millimeters in diameter. This beam is caused to scan in a direction within a plane perpendicular to the beam axis (for example, x-y plane, if defining the beam axis as z) by the scanning electromagnet 41, so that an irradiation field is formed in an extending direction of the plane. Further, because of being scattered by the scatterer 42, the beam is adjusted in its width. The particle beam B with the irradiation field formed in the plane direction, passes through the ridge filter 43 whereby its Bragg's beak is spread according to the thickness of a slice, so that the beam becomes to have a Bragg's peak spread out to a predetermined width (SOBP: Spread-Out Bragg Peak).

Then, the particle beam B passes through the range shifter 44. As the range shifter 44, an acrylic or like plate having a predetermined thickness is disposed in the irradiation region, so that the energy of the particle beam B is adjusted to be attenuated. Although the energy of the particle beam B is adjusted by the accelerator 10, it is troublesome to tune the operation patterns of the accelerator 10 as described above. As a result, a pitch for adjusting the energy by the accelerator 10 may become larger than the thickness of a slice. Thus, by finely adjusting the energy of the particle beam B by means of the range shifter 44, it is possible to irradiate (to impart dose in) an intended slice (in-body depth).

In the case of performing irradiation by a layer-stacking conformal irradiation method using the irradiation device 40 as described above, the dose injection is made such that spatially-imparted dose is given as being divided in the depth direction. At the initiation of irradiation, the operation pattern of the accelerator 10 is selected in conformity to the irradiation condition for a layer (slice) including a deepest portion, and with respect to that operation pattern, the scanning electromagnet 41 and the range shifter 44 are set capable of forming the irradiation field for that slice, whereby the patient B is irradiated with the particle beam B. After completion of irradiation to the layer (slice) at the deepest portion, the operation pattern of the accelerator 10 is selected automatically in conformity to the irradiation condition for a slice at a position shallower (a near side viewed from irradiation source) by a depth corresponding to SOBP, and with respect to that operation pattern, the scanning electromagnet 41 and the range shifter 44 are set capable of forming the irradiation field for that slice, whereby the patient K is irradiated with the particle beam B. Thereafter, while sequentially shifting a slice, each dose is similarly imparted in conformity to the three-dimensional shape of the deceased site as a whole.

A controlling operation in the series of irradiation will be described using a flowchart in FIG. 5 and a graph of operation pattern in FIG. 6.

First, the irradiation condition reading section 22 reads the irradiation condition including an irradiation angle, a number of slices, an irradiation shape/dose for each slice and the like, that is retained in the irradiation condition retaining section 24 (Step S10). Note that the irradiation condition is not necessarily retained in the control unit 20, and may be acquired through communication, etc. Then, like the above case of initiating from the deepest portion, for example, the main control section 21 sets a slice to be irradiated firstly from the read irradiation condition (Step S20). Then, the operation pattern selection section 23 selects the operation pattern suitable for the irradiation condition for that slice from among the operation patterns retained in the operation pattern retaining section 25 (Step S30). Then, the main control section 21 controls the accelerator 10 to operate in the selected operation pattern, and controls the transport system 30 and the irradiation device 40 in response to the emission of the particle beam B from the accelerator 10 according to the operation pattern, to thereby perform irradiation to the slice (Step S40). Thereafter, such operations are repeated up to the last slice (until "Y" is determined in Step S50).

Note that, in the case of slice shifting from a deeply-placed slice to a shallowly-placed slice, the long period pattern OP-L shown in FIG. 6(b) is selected as a default for the first slice (deepest portion). Basically, the irradiation time ToL in the long period pattern OP-L is set longer than the irradiation time Pe1 for the slice at the deepest portion to reach the completion of irradiation Ed, and thus it is possible to complete irradiation to the slice at the deepest portion in one operation period. Further, since the irradiation time Pe2 for the next slice is usually shorter than the irradiation time Pe1 for the deepest portion, it is similarly possible to complete irradiation in one operation period.

On the other hand, when irradiation goes forward to a shallower side of the slices, if the irradiation time $Pe_i$ that is required for fulfilling the dose in i-th slice, for example, becomes shorter than the irradiation time ToS in the short period pattern OP-S, then the short period pattern OP-S is selected. Since the irradiation time $Pe_{i+1}$ required for fulfilling the dose in the subsequent slice ((i+1)-th or later) becomes shorter and shorter basically, the short period pattern OP-S is similarly selected therefor.

This makes the waiting time in the period shorter as compared to the case where, for example, the long period pattern OP-L is selected for all slices, to thereby shorten the treatment time as a whole. Or, if the short period pattern OP-S is selected for all slices, irradiation to a deeply-placed slice will not completed in one period, resulting in a case of performing plural separate irradiation, so that the treatment time becomes longer; however, according to this embodiment, it is possible to make the treatment time shorter as a whole, because the number of the periods per one slice is totally reduced. This effect is also successful when the irradiation time ToL in the long period pattern OP-L is set shorter than the irradiation time Pe1 for the slice at the deepest portion to reach the completion of irradiation Ed.

Note that in the above example, for simplification's sake, the description is made to a case of having two operation pattern; however, the invention is not limited thereto. Further segmentalized operation patterns may be prepared by taking time and effort for tuning, etc. Further, the selection of the operation pattern is not necessarily made according to the result of comparing the period and the irradiation time as described above. For example, the selection may be made according to an energy range of the particle beam in such a manner that the operation pattern is switched when the energy can not be adjusted solely by the attenuated amount by the range shifter 44.

Modified Example of Embodiment 1

Note that the above example is described for a case where the long period pattern is made larger in energy than the short period pattern, namely, a case of retaining the operation patterns in which different periods are given for different energy. In contrast, in the modified example, there are prepared such operation patterns in which different periods are given for the same energy.

Figure 7:
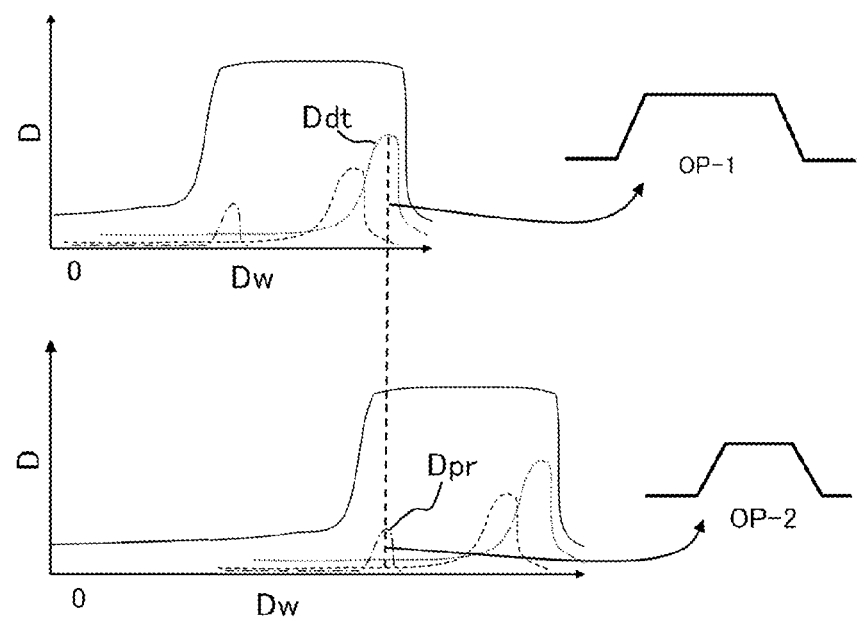
FIG. 7 is graphs showing two operation patterns of an accelerator according to an example applying Embodiment 1 of the invention.

FIG. 7 is for illustrating an embodiment that applies the modified example, and for illustrating, as an example, a relationship between an in-body depth and a imparted dose in the cases where the deceased sites of the same shape are placed in different depths, and operation patterns to be applied therefor. In the figure, the upper side shows a dose distribution for the case where the deceased site is shallowly placed from a body surface, and the lower side shows a dose distribution for the case where the deceased site is deeply placed from a body surface. The broken line connecting between the upper side and the lower side represents a position of the same depth from each body surface, namely, a same-energy requiring position. There are exemplified at the position, in the upper side, an operation pattern OP-1 corresponding to a slice that requires a long irradiation time is held because of the position being a deepest portion and thus requiring a large dose, and in the lower side, an operation pattern OP-2 corresponding to a slice that requires just a short irradiation time is held because of the position being a shallowest portion and thus requiring a small dose.

In such cases, by having prepared a plurality of operation patterns with different lengths with respect, for example, to same energy or near energy, it is possible to accurately perform irradiation with a short treatment time through selection of the operation pattern that is more suitable for the irradiation condition for a slice.

As described above, the particle beam therapy system 1 according to Embodiment 1 is configured to include: the accelerator 10 having an electromagnet (for example, deflection electromagnet 13) using a core of a magnetic material, that emits the particle beam B after adjusting it to have a given energy; the irradiation device 40 that irradiates an irradiation target with the particle beam B supplied from the accelerator 10, according to a shape of the target; and the control unit 20 that controls the accelerator 10 and the irradiation device 40 in their cooperative manner; wherein the control unit 20 is provided with: the operation pattern retaining section 25 that retains the plurality of operation patterns OP-L, OP-S each given as a pattern OP of operation to be periodically repeated by the accelerator 10, said operation patterns having respective operation conditions adjusted to have different times (irradiation times) To that allow emission of the particle beam B, and to cause the deflection electromagnet 13 in the accelerator 10 to have an intended magnetic field intensity even under a presence of a hysteresis of the magnetic material; the irradiation condition reading section 22 for a plurality of slices resulted from partitioning the irradiation target in a depth direction, that reads an irradiation condition for each of the slices; the operation pattern selection section 23 that selects the operation pattern suitable for said one of the slices from among the plurality of operation patterns, on the basis of the irradiation condition read by the irradiation condition reading section 22; and the main control section 21 that controls, for each of the slices, the accelerator 10 on the basis of the selected operation pattern and the irradiation device 40 on the basis of the irradiation condition. Thus, it is possible to select an optimum operation pattern capable of providing an intended magnetic-field intensity for each slice, and thus to make the treatment time shorter and to perform accurate irradiation.

In particular, the operation pattern selection section 23 is configured to select an operation pattern from among the plurality of operation patterns OP-S, OP-L, said operation pattern having a shortest time To that allows emission of the particle beam B among the operation patterns with which a smaller number of periods is required for imparting a dose in the relevant slice (for example, the operation patterns capable of imparting the dose in one period). Thus, it is possible to make irradiation shortest to each slice.

Further, in the plurality of operation patterns, at least two of the operation patterns OP-S, OP-L are set so that the operation pattern OP-L thereamong that is set larger in the given energy, is longer in length of time To that allows emission of the particle beam B. Thus, it is possible to make the treatment time shorter as a whole, in such a manner that, for a deeply-placed slice, the operation pattern that is capable of fulfilling a required dose in a small number of periods while ensuring the dose through emission, is established, and for a shallowly-placed slice, the operation pattern that is capable of completing irradiation in a short time, is established.

Furthermore, at least two of the operation patterns OP-1, OP-2 are set the same in the given energy and different in the time that allows emission of the particle beam B. Thus, it is possible to make the treatment time shorter as a whole, even for the slices at the same position from a body surface in the deceased sites, in such a manner that, for the slice corresponding to the deep portion, the operation pattern OP-1 that is capable of fulfilling a required dose with a small number of periods while ensuring the dose through emission, is established, and, for the slice at the same depth but corresponding to the shallow portion, the operation pattern OP-2 that is capable of completing irradiation in a short time is established.

Meanwhile, the operation method of the particle beam therapy system 1 according to Embodiment 1 is a method of operating the particle beam therapy system 1 which comprises the accelerator 10 having an electromagnet, for example the deflection electromagnet 13, using a core of a magnetic material, that emits the particle beam B after adjusting it to have a given energy; and the operation pattern retaining section 25 that retains the plurality of operation patterns OP-L, OP-S, each given as a pattern OP of operation to be periodically repeated by the accelerator 10, said operation patterns having respective operation conditions adjusted to have different times (irradiation times) To that allow emission of the particle beam B, and to cause the deflection electromagnet 13 in the accelerator 10 to have an intended magnetic field intensity even under a presence of a hysteresis of the magnetic material; said method of operating the particle beam therapy system being configured to include: the irradiation condition reading step S10 for a plurality of slices resulted from partitioning the irradiation target in a depth direction, that reads the irradiation condition for each of the slices; the operation pattern selection step S30 that selects the operation pattern suitable for said one of the slices from among the plurality of operation patterns OP-S, OP-L, on the basis of the irradiation condition read by the irradiation condition reading step S10; and the step S40 that controls, for each of the slices, the accelerator 10 on the basis of the selected operation pattern. Thus, an intended magnetic-field intensity is provided for each slice, and therefore, it is possible to make the treatment time shorter and to perform accurate irradiation.

DESCRIPTION OF REFERENCE NUMERALS AND SIGNS

1: particle beam therapy system,
10: accelerator (13: deflection electromagnets (electromagnets having cores of magnetic material),
20: control unit (21: main control section, 22: irradiation condition reading section, 23: operation pattern selection section, 24: irradiation condition retaining section, 25: operation pattern retaining section),
40: irradiation device,
OP: operation pattern (OP-L: long period pattern, OP-S: short period pattern),
To: time that allows emission (irradiation) of a particle beam in one period).

The invention claimed is:

1. A particle beam therapy system comprising:
an accelerator having a deflection electromagnet using a core of a magnetic material, that emits a particle beam after adjusting it to have a given energy;
an irradiation device that irradiates an irradiation target with the particle beam supplied from the accelerator, according to a shape of the target; and
a control unit that controls the accelerator and the irradiation device in a cooperative manner;
wherein the control unit is provided with:
an operation pattern retaining section that retains a plurality of operation patterns each being a pattern of operation to be periodically repeated by the accelerator, said operation patterns having respective operation conditions adjusted to have different times that allow emission of the particle beam, and to cause the deflection electromagnet in the accelerator to have an intended magnetic field intensity even under a presence of a hysteresis of the magnetic material;
an irradiation condition reading section for a plurality of slices resulting from partitioning the irradiation target in a depth direction, that reads an irradiation condition for each of the slices;
an operation pattern selection section that selects the operation pattern suitable for each of the slices from among the plurality of operation patterns, on the basis of the irradiation condition read by the irradiation condition reading section; and
a main control section that controls, for each of the slices, the accelerator on the basis of the selected operation pattern and the irradiation device on the basis of the irradiation condition.

2. The particle beam therapy system of claim 1, wherein the operation pattern selection section selects the operation pattern from among the plurality of operation patterns, said operation pattern having a shortest time that allows emission of the particle beam among the operation patterns with which a smaller number of periods is required for imparting a dose in each of the slices.

3. The particle beam therapy system of claim 2, wherein, in the plurality of operation patterns, at least two of the operation patterns are set so that the operation pattern there among that is set larger in the given energy, is longer in the time that allows emission of the particle beam.

4. The particle beam therapy system of claim 3, wherein, in the plurality of operation patterns, at least two of the operation patterns are set the same in the given energy and different in the time that allows emission of the particle beam.

5. The particle beam therapy system of claim 2, wherein, in the plurality of operation patterns, at least two of the operation patterns are set the same in the given energy and different in the time that allows emission of the particle beam.

6. The particle beam therapy system of claim 1, wherein, in the plurality of operation patterns, at least two of the operation patterns are set so that the operation pattern there among that is set larger in the given energy, is longer in the time that allows emission of the particle beam.

7. The particle beam therapy system of claim 6, wherein, in the plurality of operation patterns, at least two of the operation patterns are set the same in the given energy and different in the time that allows emission of the particle beam.

8. The particle beam therapy system of claim 1, wherein, in the plurality of operation patterns, at least two of the operation patterns are set the same in the given energy and different in the time that allows emission of the particle beam.

9. A method of operating a particle beam therapy system which comprises an accelerator having a deflection electromagnet using a core of a magnetic material, that emits a particle beam after adjusting it to have a given energy, and an operation pattern retaining section that retains a plurality of operation patterns each being a pattern of operation to be periodically repeated by the accelerator, said operation patterns having respective operation conditions adjusted to have different times that emission of the particle beam, and to cause the deflection electromagnet in the accelerator to have an intended magnetic field intensity even under a presence of a hysteresis of the magnetic material, said method of operating the particle beam therapy system comprising:

an irradiation condition reading step for a plurality of slices resulting from partitioning an irradiation target in a depth direction, that reads an irradiation condition for each of the slices;

an operation pattern selection step that selects the operation pattern suitable for each of the slices from among the plurality of operation patterns, on the basis of the irradiation condition read by the irradiation condition reading step; and a step that controls, for each of the slices, the accelerator on the basis of the selected operation pattern.

* * * * *